United States Patent [19]

Abatjoglou et al.

[11] Patent Number: 4,716,250

[45] Date of Patent: Dec. 29, 1987

[54] HYDROFORMYLATION USING LOW VOLATILE/ORGANIC SOLUBLE PHOSPHINE LIGANDS

[75] Inventors: Anthony G. Abatjoglou, Charleston; David R. Bryant, South Charleston, both of W. Va.

[73] Assignee: Union Carbide Corporation, Danbury, Conn.

[21] Appl. No.: 884,197

[22] Filed: Jul. 10, 1986

[51] Int. Cl.$^4$ ............................................. C07C 45/50
[52] U.S. Cl. .................................................... 568/454
[58] Field of Search ................................ 568/454, 909

[56] References Cited

U.S. PATENT DOCUMENTS

| | | | |
|---|---|---|---|
| Re. 31,812 | 1/1985 | Kuntz | 568/454 |
| 3,527,809 | 9/1970 | Pruett et al. | 568/454 |
| 3,959,385 | 5/1976 | Juergen et al. | 568/454 |
| 4,148,830 | 4/1979 | Pruett et al. | 568/454 |
| 4,247,486 | 1/1981 | Brewester et al. | 568/454 |
| 4,248,802 | 2/1981 | Kuntz . | |
| 4,283,562 | 8/1981 | Billig et al. | 568/454 |
| 4,283,563 | 8/1981 | Kawabata et al. | 568/454 |
| 4,399,312 | 8/1983 | Russell | 456/454 |
| 4,400,548 | 9/1983 | Abatjoglous et al. | 568/454 |
| 4,483,801 | 11/1984 | Sabot | 260/505 C |
| 4,483,802 | 11/1984 | Gartner et al. | 260/505 C |
| 4,504,588 | 3/1985 | Gartner et al. | 502/24 |
| 4,510,332 | 4/1985 | Matsumoto et al. | 568/454 |
| 4,523,036 | 6/1985 | Cornils et al. | 568/454 |
| 4,578,523 | 3/1986 | Bahrmann et al. | 568/454 |
| 4,593,126 | 1/1986 | Carnils et al. | 568/454 |
| 4,593,127 | 6/1986 | Bunning et al. | 568/454 |

FOREIGN PATENT DOCUMENTS

| | | | |
|---|---|---|---|
| 766804 | 5/1971 | Belgium . | |
| EP144745 | 3/1984 | European Pat. Off. | 568/454 |
| EP103810 | 3/1984 | European Pat. Off. . | |
| EP106379 | 4/1984 | European Pat. Off. | 568/454 |
| EP133410 | 6/1984 | European Pat. Off. | 568/454 |
| EP147824 | 12/1984 | European Pat. Off. | 568/454 |
| EP157316 | 3/1985 | European Pat. Off. | 568/454 |
| EP158246 | 3/1985 | European Pat. Off. | 568/454 |
| EP158572 | 3/1985 | European Pat. Off. | 568/454 |
| EP160249 | 4/1985 | European Pat. Off. | 568/454 |
| EP163233 | 5/1985 | European Pat. Off. | 568/454 |
| EP163234 | 5/1985 | European Pat. Off. | 568/454 |
| 3347406 | 3/1983 | Fed. Rep. of Germany . | |
| 3411034 | 9/1985 | Fed. Rep. of Germany . | |
| 83-05374 | 3/1982 | Spain . | |

OTHER PUBLICATIONS 2,478,078, (1981), French Patent No.

Primary Examiner—Werren B. Lone
Attorney, Agent, or Firm—R. J. Finnegan

[57] ABSTRACT

A nonaqueous hydroformylation process for producing aldehydes using low volatile, organic soluble monosulfonated tertiary phosphine salt ligands.

19 Claims, No Drawings

HYDROFORMYLATION USING LOW VOLATILE/ORGANIC SOLUBLE PHOSPHINE LIGANDS

TECHNICAL FIELD

This invention relates to transition metal-phosphorus complex catalyzed hydroformylation using monosulfonated tertiary phosphine salt ligands. More particularly this invention relates to the rhodium-monosulfonated tertiary phosphine salt ligand complex catalyzed non-aqueous hydroformylation of olefinic compounds to their corresponding aldehydes.

BACKGROUND OF THE ART

The hydroformylation of an olefinic compound with carbon monoxide and hydrogen to produce aldehydes using an organic solubilized transition metal-phosphorus ligand complex catalyst is well known in the art.

It is further well known that the phosphorus ligand employed in such catalyzed hydroformylation processes may have a direct effect on the success of such a given process. Moreover, the selection of the particular phosphorus ligand to be used in any such transition metal catalyzed hydroformylation process depends in the main on the end result desired, since the best overall processing efficiency may require a compromise between numerous factors involved. For example, in hydroformylation such factors as aldehyde product selectivity (i.e., normal to branched chain aldehyde product ratios), catalyst reactivity and stability, and ligand stability are often of major concern in the selection of the desired phosphorus ligand to be employed. For instance, U.S. Pat. No. 3,527,809 teaches how alpha olefins can be selectively hydroformylated with rhodium-triorganophosphine or triorganophosphite ligand complexes to produce oxygenated products rich in normal aldehydes, while U.S. Pat. Nos. 4,148,830 and 4,247,486 disclose both liquid and gas recycle operations directed to the same result using a rhodium triarylphosphine ligand complex catalyst. U.S. Pat. No. 4,283,562 discloses that branched-alkylphenylphosphine or cycloalkylphenylphosphine ligands can be employed in a rhodium catalyzed hydroformylation process in order to provide a more stable catalyst against intrinsic deactivation. U.S. Pat. No. 4,400,548 discloses that bisphosphine monoxide ligands can be employed to provide rhodium complex catalysts of improved thermal stability useful for the hydroformylation production of aldehydes.

However, despite the obvious benefits attendant with the prior art references mentioned above, the search continues for phosphorus ligands which will more effectively satisfy additional ligand requirements, particularly with regard to ligand volatility.

For example, rhodium complex catalyzed hydroformylation processes are preferably carried out in a non-aqueous hydroformylation reaction medium containing both the soluble catalyst complex and free excess phosphorus ligand, i.e., ligand not tied to or bound to the rhodium complex. In such processes the desired aldehyde product is preferably separated and recovered from the reaction product medium by distillation, and in the case of continuous liquid catalyst recycle operations, the non volatilized catalyst ligand containing residue is recycled to the reactor. Accordingly, an important requirement of such processes is the effective separation and recovery of the desired aldehyde product from its hydroformylation reaction product medium without excessive phosphorus ligand and/or catalyst complex loss. Thus in such non-aqueous hydroformylation processes, and in particular liquid catalyst recycle processes, the volatility of the phosphorus ligand is also of primary concern, since continuous removal (stripping) of the phosphorus ligand during aldehyde product separation via distillation can result not only in high phosphorus ligand loss which must be replaced, but can also lead to changes in the catalyst properties and even eventual catalyst deactivation. Indeed, if the rate of such simultaneous volatilization of the phosphorus ligand is too high an additional ligand recovery/recycle scheme may be required in order for the process to be economical.

While, this problem of ligand volatility (re aldehyde product separation) in non aqueous hydroformylation may not be as overwhelming when low molecular weight olefins, such as propylene, are hydroformylated, using conventional tertiary phosphines such as triphenylphosphine, it is still of some concern and said problem increases and magnifies when the process is directed to the hydroformylation of long chain olefinic compounds (e.g., $C_6$ to $C_{20}$ alpha-olefins) to produce their corresponding higher molecular weight aldehydes due to the high temperatures necessary to volatilize such high molecular weight aldehyde products from the hydroformylation reaction product medium. Likewise ligand loss due to volatility, when higher boiling aldehyde condensation by products, such as trimers, etc., are desired to be removed e.g. from catalyst containing hydroformylation residues, in order to recover such catalysts and ligands is also of major concern to the art regardless of whether or not such aldehyde condensation by products are the result of hydroformylating low (e.g. $C_2$–$C_5$) or high (e.g. $C_6$–$C_{20}$) molecular weight olefins.

It has been proposed to use aqueous solutions of sulfonated aryl phosphine compounds as the phosphorus ligand, such as the sulfonated triphenylphosphine salts disclosed e.g., in EPC No. 163234 and U.S. Pat. Nos. 4,248,802, 4,399,312, and the like, as the phosphorus ligand in the hydroformylation process to facilitate the separation and recovery of the rhodium complex catalyst. However, all such prior art methods also involve the employment of an aqueous hydroformylation reaction medium made up of both an organic phase containing the reaction starting materials and/or products and an aqueous or water phase containing the catalyst complex and sulfonated phosphine ligands, in contrast to a non-aqueous hydroformylation reaction medium. Moreover, such aqueous or water phase type hydroformylation systems in general require high reactor pressures and/or high rhodium concentrations and may also require buffers or phase transfer reagents and/or the use of larger and more costly processing apparatus equipment.

Therefore there is a definite need in the hydroformylation art for low volatile/organic soluble phosphorus ligands which will function effectively in a non-aqueous rhodium catalyzed hydroformylation process with regard to hydroformylating both low molecular weight olefins (e.g., $C_2$ to $C_5$ olefins) and in particular long chain, high molecular weight olefinic compounds, (e.g., $C_6$ to $C_{20}$ olefins).

DISCLOSURE OF THE INVENTION

It has now been discovered that certain monosulfonated tertiary phosphine salt ligands may be employed as the phosphorus ligand in non-aqueous Group VIII transition metal-phosphorus complex catalyzed hydroformylation processes to provide numerous advantages.

For instance, the monosulfonated tertiary phosphine salt ligands employable herein are water-insoluble, but organically soluble, and therefore especially suitable for use as the phosphorus ligand in non-aqueous rhodium catalyzed hydroformylation processes designed to produce aldehyde products from both low and high molecular weight olefinic compounds. Due to the organic solubility and low volatility of such monosulfonated tertiary phosphine salt ligands, separation of the aldehyde product from the rhodium complex catalyst containing reaction product medium may be easily accomplished by vaporization (distillation) even when the non-aqueous hydroformylation process is directed to producing such high molecular weight aldehyde products as those derived from the hydroformylation of long chain olefins of $C_6$ to $C_{20}$ carbon atoms without undue ligand and/or catalyst loss. Moreover, the monosulfonated tertiary phosphine salt ligands employable herein help promote the rhodium catalyzed hydroformylation of both low and high molecular weight olefins at highly acceptable catalyst activity rates even at conventional low hydroformylation pressures (e.g., less than 500 psig.) and/or with low rhodium concentrations without unduly sacrificing processing efficiency and/or catalyst stability. Furthermore, the monosulfonated tertiary phosphine salt ligands employable herein have not been observed to unduly, adversely promote aldehyde by product heavies formation. Moreover, the non-aqueous hydroformylation process of this invention involving the hydroformylation of high molecular weight ($C_6$ to $C_{20}$) olefins can be readily retrofitted to existing non-aqueous hydroformylation design apparatus and equipment conventionally employed to hydroformylate low molecular weight ($C_2$ to $C_5$) olefins, without the need for major modifications of same.

Another unexpected advantage of the monosulfonated tertiary phosphine salt ligands employable in this invention is that the straight (normal) chain to branched (iso) chain aldehyde product ratio (selectivity) of the hydroformylation process can be varied over a wide range by simply varying the type and size of the cation group of such ligands, in addition to being able to vary said aldehyde product ratio by adjusting carbon monoxide partial pressure and/or phosphine ligand concentration. Such normal to iso (N/I) selectivity control is of significant importance in hydroformylation in as much as it allows one to maximize the yield of whichever particular aldehyde product is desired. Moreover, such control in being able to vary the N/I aldehyde product ratios may be achieved herein without unduly adversely effecting the process efficiency and/or catalyst stability of the process.

Thus it is an object of this invention to provide an improved hydroformylation process wherein said process is carried out in an organic, non-aqueous hydroformylation reaction medium containing an organic solubilized Group VIII transition metal-monosulfonated tertiary phosphine salt ligand complex catalyst. Other objects and advantages of this invention will become readily apparent from the following written description and appended claims.

Accordingly, a generic aspect of this invention can be described as an improved non-aqueous hydroformylation process for producing aldehydes which comprises reacting an olefinically unsaturated organic compound with carbon monoxide and hydrogen, in a non-aqueous hydroformylation reaction medium containing an organic solubilized Group VIII transition metal phosphorus ligand complex catalyst and free phosphorus ligand, the improvement comprising employing as the phosphorus ligand of said complex catalyst and as said free phosphorus ligand, an organic soluble monosulfonated tertiary phosphine salt having the general formula

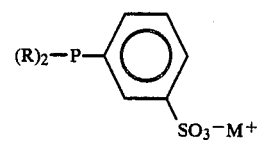

wherein each R group individually represents a radical containing from 1 to 30 carbon atoms selected from the class consisting of alkyl, aryl, alkaryl, aralkyl and cycloalkyl radicals and M represents an amine cation having the general formula

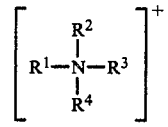

wherein $R^1$ represents hydrogen or a radical containing from 1 to 3 carbon atoms selected from the class consisting of alkyl, aryl, alkaryl, aralkyl, and cycloalkyl radicals, and each $R^2$, $R^3$ and $R^4$ group individually represents a radical containing from 1 to 3 carbon atoms selected from the class consisting of alkyl, aryl, alkaryl, aralkyl and cyclohexyl radicals, and wherein any two or three of said $R^1$, $R^2$, $R^3$ and $R^4$ groups can be bonded together to form a mono-, bi-, or poly-cyclic ring along with the nitrogen atom of said amine cation; with the proviso that in any given monosulfonated tertiary phosphine salt employed at least one of said $R^1$, $R^2$, $R^3$ and $R^4$ groups of the amine cation, M, represents an alkyl or aralkyl radical containing from 8 to 30 carbon atoms.

DETAILED DESCRIPTION

Accordingly, the subject invention encompasses the carrying out of any known non-aqueous, hydroformylation process for producing aldehydes by reacting an olefinically unsaturated compound with carbon monoxide and hydrogen in a non-aqueous hydroformylation reaction medium containing an organic solubilized Group VIII transition metal-phosphorus ligand complex catalyst and free phosphorus ligand in which both the phosphorus ligand of said catalyst and free phosphorus ligand is replaced by an organic soluble monosulfonated tertiary phosphine salt ligand as disclosed herein. Such generic hydroformylation (oxo synthesis) processes are well known in the art as seen for example by U.S. Pat. Nos. 3,527,809; 4,148,830; 4,247,486 and the like. Accordingly, the reaction conditions and processing techniques of this invention may correspond if desired to any of the known reaction conditions and processing techniques heretofore employed in such conventional hydroformylation reactions.

For instance, the hydroformylation process can be conducted in continuous, semi-continuous, or batch fashion and involve any liquid and/or gas recycle operation, as desired. Likewise, the manner or order of addition of the reaction ingredients, catalyst, ligand, and/or solvent may be accomplished in any conventional fashion.

As noted, the hydroformylation reaction is carried out in a non-aqueous, organic hydroformylation reaction medium that contains both the organic solubilized Group VIII transition metal-monosulfonated tertiary phosphine salt ligand complex catalyst and free monosulfonated tertiary phosphine salt ligand. By "free ligand" is meant phosphorus ligand that is not complexed with (tied to or bound to) the Group VIII transition metal atom in the active complex catalyst. Moreover, the term "non-aqueous" as employed in this invention means that the hydroformylation process of this invention is conducted, in the absence or essential absence of water, which is to say that any water, if present at all, in the hydroformylation reaction medium, is not present in an amount sufficient to cause the process to be considered as encompassing an aqueous or water phase in addition to an organic phase.

As noted above the monosulfonated phosphine salt ligands employable in this invention are those having the formula

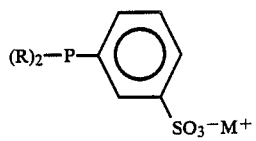

wherein each R and M, are the same as defined above.

Illustrative radicals represented by the R groups in the above monosulfonated tertiary phosphine salt ligand formulas include both unsubstituted and substituted monovalent hydrocarbon radicals containing from 1 to 30 carbon atoms, e.g., alkyl radicals including linear or branched, primary, secondary or tertiary alkyl radicals, such as methyl, ethyl, n-propyl, isopropyl, butyl, sec-butyl, t-butyl, t-butylethyl, t-butylpropyl, n-hexyl, amyl, sec-amyl, t-amyl, 2-ethylhexyl, n-octyl, iso-octyl, decyl, dodecyl, octadecyl, eicosyl and the like; aryl radicals such as phenyl, naphthyl, and the like; aralkyl radicals such as benzyl, phenylethyl, tri-phenylmethylethane, and the like; alkaryl radicals such as tolyl, xylyl, and the like; and alicyclic radicals such as cyclopentyl, cyclohexyl, cyclooctyl, cyclohexylethyl, and the like. Moreover, such monovalent hydrocarbon radicals may be substituted with any substituent that does not unduly adversely effect the desired results of this invention. Illustrative substituents that may be on the hydrocarbon radicals may include for example silyl radicals such as $-Si(R^9)_3$; amino radicals such as $-N(R^9)_2$; acyl radicals such as $-C(O)R^9$, acyloxy radicals such as $-OC(O)R^9$; amido radicals such as $-CON(R^9)_2$ and $-N(R^9)COR^9$; sulfonyl radicals such as $-SO_2R^9$, alkoxy radicals such as $-OR^9$; thionyl radicals such as $-SR^9$, as well as, halogen, nitro, cyano, trifluoromethyl, and hydroxy radicals, and the like, wherein each $R^9$ individually represents the same or different substituted or unsubstituted monovalent hydrocarbon radical having the same meaning as defined for R above, with the proviso that in amino substituents such as $-N(R^9)_2$, each $R^9$ taken together can also represent a divalent bridging group that forms a heterocyclic radical with the nitrogen atom, and in amido substituents such as $-C(O)N(R^9)_2$ and $-N(R^9)COR^9$ each $R^9$ bonded to N can also be hydrogen. Of course it is to be understood that each R group in a particular given salt ligand may be the same or different.

The more preferred monovalent hydrocarbon radicals represented by R are linear or branched alkyl radicals having from $C_3$ to $C_{20}$ carbon atoms, aryl radicals having from $C_6$ to $C_{12}$ carbon atoms and alicyclic radicals having from $C_5$ to $C_{12}$ carbon atoms. Preferably each R group is individually a branched chain alkyl radical having from 3 to 9 carbon atoms, phenyl or cyclohexyl radical. Most preferably the both R radicals in a given monosulfonated tertiary phosphine salt represent a phenyl and/or cyclohexyl radical, especially phenyl.

As noted above, M in the monosulfonated tertiary phosphine salt ligand formula above, represents an amine cation. Illustrative amine cations include those of the formula

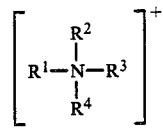

wherein $R^1$, $R^2$, $R^3$ and $R^4$ are the same as defined above including the proviso clause that at least one $R^1$, $R^2$, $R^3$ and $R^4$ group in any given monosulfonated tertiary phosphine salt ligand represents an alkyl or aralkyl radical containing from 8 to 20 carbon atoms. Such radicals represented by $R^1$, $R^2$, $R^3$ and $R^4$ also include both substituted or unsubstituted monovalent hydrocarbon radicals containing from 1 to 30 carbon atoms and such may be illustrated by the same radicals and substituents shown above for the R groups of the generic salt ligand formulas. Of course as noted above, $R^1$ may also be hydrogen. It is to be also understood that each $R^1$, $R^2$, $R^3$ and $R^4$ group may be the same or different in any given monosulfonated tertiary phosphine salt. Moreover any two or three of said $R^1$, $R^2$, $R^3$ and $R^4$ groups may be bonded together to form a mono-, bi-, or poly cyclic ring having from 4 to 30 carbon atoms along with the nitrogen atom of said amine cation. Illustrative mono-, bi-, or poly-cyclic rings that might be formed when any two or three $R^1$, $R^2$, $R^3$ and $R^4$ groups are bonded together along with the nitrogen atom of the amine cation include e.g., N-dodecylpiperidine, and the like. Illustrative long chain alkyl or aralkyl radicals containing from 8 to 30 carbon atoms of said proviso clause for the $R^1$, $R^2$, $R^3$ and $R^4$ groups include e.g., linear or branched chain alkyl radicals such as octyl, iso-octyl, 2-ethylhexyl, decycl, dodecyl, octadecyl, eicosyl, and the like and aralkyl radicals such as phenylethyl and the like. Preferably M is an amine cation wherein $R^1$ is hydrogen or an alkyl radical containing from 1 to 20 carbon atoms, $R^2$ and $R^3$ are alkyl radicals containing from 1 to 20 carbon atoms and $R^4$ is a long chain alkyl or aralkyl radical containing from 8 to 20 carbon atoms.

A preferred class of monosulfonated tertiary phosphine salt ligands employable herein are those having the formula

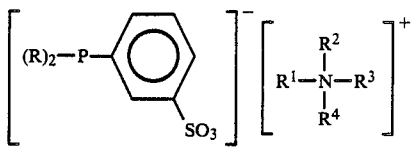

wherein each R individually represents a radical selected from the group consisting of alkyl radicals containing from 3 to 20 carbon atoms (especially secondary branched chain alkyl radicals having from 3 to 9 carbon atoms such as isopropyl, t-butyl, etc.), phenyl and cyclohexyl radicals, wherein $R^1$ is hydrogen or an alkyl radical containing from 1 to 20 carbon atoms, more preferably 1 to 8 carbon atoms, wherein $R^2$ and $R^3$ are each individually alkyl radicals containing from 1 to 20 carbon atoms, more preferably 1 to 8 carbon atoms, and wherein $R^4$ is an alkyl radical or an aralkyl radical containing from 8 to 20 carbon atoms, more preferably from 8 to 16 carbon atoms. Most preferably $R^1$ is hydrogen, both R groups are phenyl and/or cyclohexyl, especially phenyl, $R^2$ and $R^3$ are each individually alkyl radicals containing from 1 to 8 carbon atoms, and $R^4$ is an alkyl radical containing from 8 to 16 carbon atoms.

Illustrative preferred monosulfonated tertiary phosphine salt ligands include e.g., those having the following general formulas:

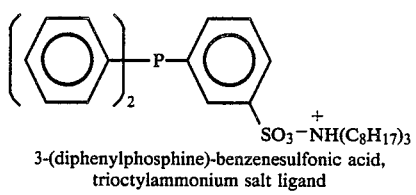

3-(diphenylphosphine)-benzenesulfonic acid, trioctylammonium salt ligand

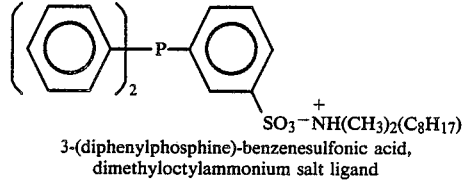

3-(diphenylphosphine)-benzenesulfonic acid, dimethyloctylammonium salt ligand

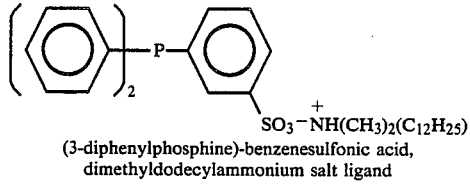

(3-diphenylphosphine)-benzenesulfonic acid, dimethyldodecylammonium salt ligand

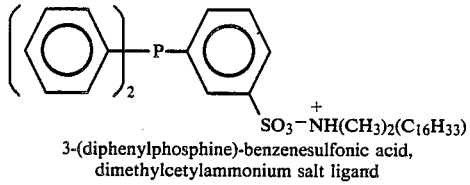

3-(diphenylphosphine)-benzenesulfonic acid, dimethylcetylammonium salt ligand

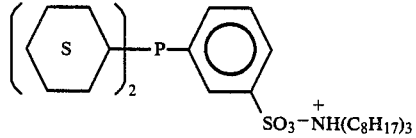

3-(dicyclohexylphosphine)-benzenesulfonic acid, trioctylammonium salt ligand

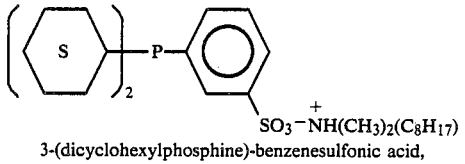

3-(dicyclohexylphosphine)-benzenesulfonic acid, dimethyloctylammonium salt ligand

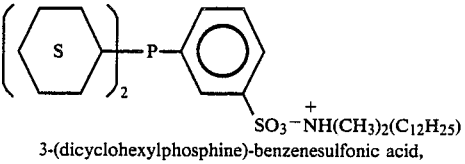

3-(dicyclohexylphosphine)-benzenesulfonic acid, dimethyldodecylammonium salt ligand

3-(dicyclohexylphosphine)-benzenesulfonic acid, dimethylcetylammonium salt ligand

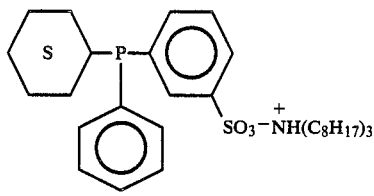

3-(cyclohexylphenylphosphine)-benzenesulfonic acid, trioctylammonium salt ligand

3-(cyclohexylphenylphosphine)-benzenesulfonic acid, dimethyldodecylammonium salt ligand

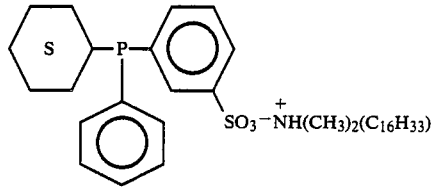

3-(cyclohexylphenylphosphine)-benzenesulfonic acid, dimethylcetylammonium salt ligand

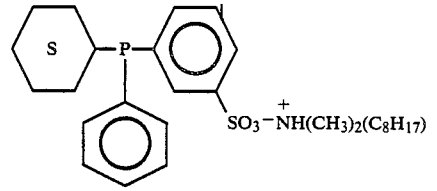

3-(cyclohexylphenylphosphine)-benzenesulfonic acid, dimethyloctylammonium salt ligand -continued

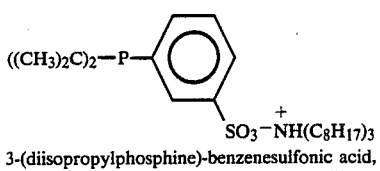

3-(diisopropylphosphine)-benzenesulfonic acid, trioctylammonium salt ligand, and the like.

Such types of monosulfonated tertiary phosphine salt ligands employable in this invention and/or methods for their manufacture are well known, as seen e.g., by the procedures described in "J. Chem. Soc.", pp. 276–288 (1958) and U.S. Pat. No. 4,483,802. Preferably such ligands are prepared by sulfonating a corresponding phenyl containing tertiary phosphine, e.g.,

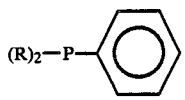

wherein R is the same as defined above with fuming sulfuric acid (oleum) under controlled temperature conditions to form predominately the corresponding protonated monosulfonated phenyl containing tertiary phosphine, e.g.,

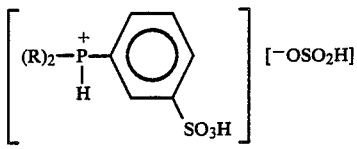

For instance, the solid phosphine is added to the fuming sulfuric acid in portions while controlling the temperature below 30° C. and then heated, e.g., to 70°–80° C. until an aliquot from the reaction mixture does not show turbidity. The reaction mixture is then cooled immediately to stop any further sulfonation and without waiting added to water while controlling the temperature below 30° C. and said protonated phosphine salt then neutralized with concentrated sodium hydroxide to form the corresponding water-insoluble monosulfonated phenyl containing tertiary phosphine sodium salt precipitate, e.g.,

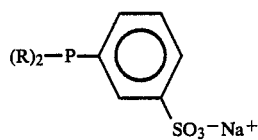

and by-product sodium sulfate. (Any di- and/or trisulfonated phosphine salts are water-soluble and remain in solution.) The tertiary phosphine sodium monosulfonate precipitate is then recovered after filtration by extracting it from the sodium sulfate with methanol, followed by evaporation of the methanol. The crude tertiary phosphine sodium monosulfonate precipitate is then purified by dissolving it in a suitable solvent such as water or ethanol and recrystallizing it therefrom. The purified tertiary phosphine sodium monosulfonate is then converted to its corresponding monosulfonic acid e.g.,

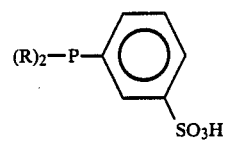

via conventional ion exchange by dissolving the purified tertiary phosphine sodium monosulfonate in a suitable solvent such as methanol or water and passing the solution over an acid anion exchange resin bed, e.g., Amberlite ® IR-120H (Rohm and Haas). The solubilized tertiary phosphine monosulfonic acid is then treated (neutralized) with a corresponding amine base e.g., a corresponding tertiary amine or quaternary ammonium hydroxide (containing at least one alkyl or aralkyl radical having from $C_8$ to $C_{30}$ carbon atoms in order to satisfy the proviso clause of the monosulfonated tertiary phosphine salt ligands employable in this invention) in a suitable solvent such as methanol, to arrive at, the desired monosulfonated tertiary phosphine salt ligand e.g.,

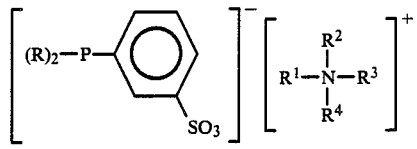

employable in this invention, which is easily recovered, e.g., by evaporation of the solvent. Of course it is understood that each R, $R^1$, $R^2$, $R^3$ and $R^4$ groups in the above formulas are the same as already herein defined above. Moreover, the employment of a corresponding tertiary amine (e.g., $R^2R^3R^4N$) will yield a desired corresponding monosulfonated tertiary phosphine salt ligand employable in this invention wherein the $R^1$ group of the amine cation of the above formulas, represents hydrogen; while desired monosulfonated tertiary phosphine salt ligands employable in this invention wherein all of the $R^1$, $R^2$, $R^3$ and $R^4$ groups of the amine cation of the above formulas are e.g., hydrocarbon radicals, are obtainable using a corresponding quaternary ammonium hydroxide (e.g., $R^1R^2R^3R^4N$-OH). Use of a quaternary ammonium hydroxide will also produce a mole of water which is removed during evaporation of the solvent.

Illustrative tertiary phosphines, tertiary amines and quaternary ammonium hydroxides that may be used to prepare the monosulfonated tertiary phosphine salt ligands employable in this invention include for example, triphenylphosphine, diphenylcyclohexylphosphine, phenyldicyclohexylphosphine, diphenylisopropylphosphine, phenyldiisopropylphosphine, diphenyltertiarybutylphosphine, and the like; trioctylamine, dimethyloctylamine, dimethyldodecylamine, dimethylcetylamine, diethyloctylamine, dimethylphenylethylamine, and the like; trimethylcetyl ammonium hydroxide, trimethyldodecyl ammonium hydroxide, tributyldodecyl ammonium hydroxide, dodecylethyldimethyl ammonium hydroxide, triethylphenylethyl ammonium hydroxide, and the like.

As in the case of prior art, non-aqueous hydroformylation processes wherein an olefin is reacted with carbon monoxide and hydrogen in a non-aqueous hydroformylation reaction medium containing an organic solubilized Group VIII transition metal (e.g., rhodium)-phosphorus ligand complex catalyst and free phosphorus ligand, the monosulfonated tertiary phosphine salt ligands and Group VIII transition metal-monosulfonated tertiary phosphine salt ligand complex catalysts employable in this invention are also organically soluble in said non-aqueous hydroformylation reaction mediums which also contain the olefin, aldehyde product and higher boiling aldehyde condensation aldehyde by-products. Indeed the monosulfonated tertiary phosphine salt ligands and Group VIII transition metal-monosulfonated tertiary phosphine salt ligand complex catalysts employable in this invention are so readily solubilized in such non-aqueous olefin, aldehyde and higher boiling aldehyde condensation by-product type hydroformylation reaction mediums, that no additional specialized solubilizing agent or aid is required to render the catalysts and ligands used in this invention soluble in the hydroformylation reaction medium, although a compatible organic co-solvent and/or solubilizing agent may be employed if desired. It is considered that this excellent organic solubility on the part of the monosulfonated tertiary phosphine salt ligands and complex catalysts employable in this invention is directly attributed to the amine cation of the phosphine salt ligands and the presence of at least one alkyl or aralkyl radical containing at least eight carbon atoms on said amine cation. Accordingly, the monosulfonated tertiary phosphine salt ligands employable in this invention can be easily employed in the same manner, as for example previous conventional triorganophosphorus ligands such as triphenylphosphine, in heretofore conventional non-aqueous hydroformylation reactions.

The Group VIII transition metals which make up the metal-monosulfonated tertiary phosphine salt ligand complexes of this invention include those selected from the group consisting of rhodium (Rh), cobalt (Co), iridium (Ir), ruthenium (Ru), iron (Fe), nickel (Ni), palladium (Pd), platinum (Pt) and osmium (Os), and mixtures thereof, with the preferred metals being Rh, Co, Ir and Ru, more preferably Rh and Co, especially Rh. It is to be noted that the successful practice of this invention does not depend and is not predicated on the exact structure of the catalytically active metal complex species, which may be present in their mononuclear, dinuclear and or higher nuclearity forms. Indeed the exact active structure is not known. Although it is not intended herein to be bound to any theory or mechanistic discourse, it appears that the active catalytic species may in its simplest form consist essentially of the Group VIII transition metal in complex combination with the carbon monoxide and monosulfonated tertiary phosphine salt ligand.

The term "complex" as used herein and in the claims means a coordination compound formed by the union of one or more electronically rich molecules or atoms capable of independent existence with one or more electronically poor molecules or atoms, each of which is also capable of independent existence. As can be surmised from the above discussion, carbon monoxide (which is also properly classified as a ligand) is also present and complexed with the Group VIII transition metal. The ultimate composition of the active complex catalyst may also contain an additional organic ligand or anion satisfying the coordination sites or nuclear charge of the Group VIII transition metal as in the case of heretofore conventional Group VIII transition metal-triorganophosphine or phosphite catalysts such as e.g., hydrogen and the like. It is of course to be understood that the active complex species is preferably free of any additional organic ligand or anion that might poison the catalyst and have an undue adverse effect on catalyst performance. For instance it is known that in conventional rhodium catalyzed hydroformylation reactions that halogen anions can poison the catalyst. Accordingly it is preferred that in the rhodium catalyzed hydroformylation reactions of this invention that the active catalysts also be free of halogen directly bonded to the rhodium.

The number of available coordination sites on such Group VIII transition metals is well known in the art and may range in number from 4 to 6. By way of illustration it appears that the preferred active rhodium catalyst species of this invention contains, in its simplest form, an amount of monosulfonated tertiary phosphine salt ligand and carbon monoxide equal to a total of four moles in complex combination with one mole of rhodium Thus the active species may comprise a complex catalyst mixture, in their monomeric, dimeric or higher nuclearity forms, which are characterized by one, two, and/or three monosulfonated tertiary phosphine salt molecules complexed per one molecule of rhodium. As noted above carbon monoxide is also present and complexed with the rhodium in the active species. Moreover, as in the case of conventional rhodium-triorganophosphine or phosphite ligand complexed catalyzed hydroformylation reactions wherein the active catalyst species is generally considered to also contain hydrogen directly bonded to the rhodium, it is likewise considered that the active species of the preferred rhodium catalyst employed in this invention during hydroformylation may also be complexed with hydrogen in addition to the monosulfonated tertiary phosphine salt and carbon monoxide ligands. Indeed it is believed that the active species of any Group VIII transition metal catalyst of this invention may also contain hydrogen in addition the monosulfonated tertiary phosphine salt and carbon monoxide ligands during hydroformylation, particularly in view of the hydrogen gas employed in the process.

Further, regardless of whether one preforms the active complex catalyst prior to introduction into the carbonylation reaction zone or whether the active species is prepared in situ during hydroformylation, the hydroformylation reaction is effected in the presence of free monosulfonated tertiary phosphine salt ligand. Thus by way of illustration the ultimate composition of the preferred active rhodium complex species catalyst can be likened or attributable to the outcome of competing reactions between carbon monoxide and the monosulfonated tertiary phosphine salt ligands for complexing or coordination sites with the rhodium element. These competing reactions can be disturbed or influenced, within significant limits, by increasing or decreasing the concentration of the monosulfonated tertiary phosphine salt ligand. As a generalized statement, the component (carbon monoxide or monosulfonated tertiary phosphine salt ligand) which can shift the equilibrium of the competing reaction in its favor should enjoy the greater opportunities of occupying the coordination or complexing sites. For example, one may view the function of free monosulfonated tertiary phosphine salt ligand as either maintaining the status quo of the various forms of active complex catalyst during the hydroformylation, or as a means for shifting the equilibrium of the competing reactions in its favor and therefore causing additional monosulfonated tertiary phosphine salt ligands to enter into complex combination with rhodium with the probable eviction of a similar number of carbon monoxide ligands from the complex catalyst.

As noted above the monosulfonated tertiary phosphine salt ligands defined above are employed in this invention as both the phosphorus ligand of the Group VIII transition metal complex catalyst, as well as, the free phosphorus ligand that is present in the reaction medium of the process of this invention. In addition, it is to be understood that while the phosphorus ligand of the Group VIII transition metal-monosulfonated tertiary phosphine salt ligand complex catalyst and excess free monosulfonated tertiary phosphine salt ligand present in a given process of this invention are normally the same, different monosulfonated tertiary phosphine salt ligands, as well as, mixtures of two or more different monosulfonated tertiary phosphine salt ligands may be employed for each purpose in any given process, if desired.

As in the case of prior art Group VIII transition metal-phosphorus complex catalysts, the Group VIII transition metal-monosulfonated tertiary phosphine salt ligand complex catalysts of this invention may be formed by methods known in the art. For instance, preformed Group VIII transition metal hydrido carbonyl monosulfonated tertiary phosphine salt ligand complex catalysts may be prepared and introduced into the reaction medium of the hydroformylation process. More preferably, the Group VIII transition metal-monosulfonated tertiary phosphine salt ligand complex catalysts of this invention can be derived from a metal catalyst precursor which may be introduced into the reaction medium for in situ formation of the active catalyst. For example, rhodium catalyst precursors such as rhodium dicarbonyl acetylacetonate, $Rh_2O_3$, $Rh_4(CO)_{12}$, $Rh_6(CO)_{16}$, $Rh(NO_3)_3$ and the like may be introduced into the reaction medium along with the monosulfonated tertiary phosphine salt ligand for the in situ formation of the active catalyst. In a preferred embodiment rhodium dicarbonyl acetylacetonate is employed as a rhodium precursor and reacted in the presence of an organic solvent with the monosulfonated tertiary phosphine salt to form a catalytic rhodium carbonyl monosulfonated tertiary phosphine salt acetylacetonate precursor which is introduced into the reactor along with excess free monosulfonated tertiary phosphine salt ligand for the in situ formation of the active catalyst. In any event, it is sufficient for the purpose of this invention to understand that carbon monoxide, hydrogen and monosulfonated tertiary phosphine salt are all ligands that are capable of being complexed with the Group VIII transition metal, e.g., rhodium and that an active Group VIII transition metal-monosulfonated tertiary phosphine salt ligand complex catalyst is present in the reaction medium under the conditions of the hydroformylation process.

Moreover, like prior art Group VIII transition metal phosphorus ligand complex catalysts it is clear that the amount of complex catalyst present in the reaction medium of a given process of this invention need only be that minimum amount necessary to provide the given Group VIII transition metal concentration desired to be employed and which will furnish the basis for at least that catalytic amount of Group VIII transition metal necessary to catalyze the hydroformylation process. In general, Group VIII transition metal concentrations in the range of from about 10 ppm to about 1000 ppm, calculated as free metal, should be sufficient for most hydroformylation processes. Moreover, in the rhodium catalyzed hydroformylation processes of this invention, it is generally preferred to employ from about 10 to 500 ppm of rhodium and more preferably from 25 to 350 ppm of rhodium, calculated as free metal.

The olefinic starting material reactants encompassed by the processes of this invention can be terminally or internally unsaturated and be of straight-chain, branched-chain or cyclic structure. Such olefins can contain from 2 to 20 carbon atoms and may contain one or more ethylenic unsaturated groups. Moreover, such olefins may contain groups or substituents which do not essentially adversely interfere with the hydroformylation process such as carbonyl, carbonyloxy, oxy, hydroxy, oxycarbonyl, halogen, alkoxy, aryl, haloalkyl, and the like. Illustrative olefinic unsaturated compounds include alpha olefins, internal olefins, alkyl alkenoates, alkenyl alkenoates, alkenyl alkyl ethers, alkenols, and the like, e.g., ethylene, propylene, 1-butene, 1-pentene, 1-hexene, 1-heptene, 1-octene, 1-nonene, 1-decene, 1-undecene, 1-dodecene, 1-tridecene, 1-tetradecene, 1-pentadecene, 1-hexadecene, 1-heptadecene, 1-octadecene, 1-nonadecene, 1-eicosene, 2-butene, 2-methyl propene (isobutylene), 2-octene, styrene, 3-phenyl-1-propene, 1,4-hexadiene, 1,7-octadiene, 3-cyclohexyl-1-butene, allyl alcohol, hex-1-en-4-ol, oc-1-en-4-ol, vinyl acetate, allyl acetate, vinyl propionate, allyl propionate, allyl butyrate, methyl methacrylate, vinyl ethyl ether, vinyl methyl ether, allyl ethyl ether, n-propyl-7-octenoate, 3-butenenitrile, 5-hexenamide, and the like. Of course, it is understood that mixtures of different olefinic starting materials can be employed, if desired, by the hydroformylation process of the subject invention. The subject invention is especially useful for the production of aldehydes, by hydroformylating alpha olefins containing from 2 to 20 carbon atoms as well as starting material mixtures of such alpha olefins and internal olefins. The preferred olefin starting materials are low molecular weight alpha olefins having from 2 to 5 carbon atoms, more preferably high molecular weight alpha olefins containing from 6 to 20 carbon atoms and most preferably high molecular weight alpha olefins having from 6 to 14 carbon atoms. It is of course to be understood that commercial alpha olefins containing 4 or more carbon atoms may also contain minor amounts of corresponding internal olefins and/or their corresponding saturated hydrocarbon and that such commercial olefins need not be purified from same prior to being employed in this invention.

As noted the hydroformylation process of this invention is also conducted in the presence of an organic solvent for the monosulfonated tertiary phosphine salt ligand and the Group VIII transition metal-monosulfonated tertiary phosphine salt ligand complex catalyst. Any suitable organic solvent which does not unduly adversely interfere with the intended hydroformylation process can be employed and such organic solvents may include those heretofore commonly employed in known Group VIII transition metal catalyzed processes. By way of illustration suitable organic solvents for rhodium catalyzed hydroformylation processes include those disclosed e.g., in U.S. Pat. Nos. 3,527,809 and 4,148,830. Of course, mixtures of one more different organic solvents may be employed if desired. In general, in rhodium catalyzed hydroformylation it is preferred to employ aldehyde compounds corresponding to the aldehyde products desired to be produced and/or higher boiling aldehyde liquid condensation by-products that are produced in situ during the hydroformylation process as the primary organic solvent. Indeed, while one may employ, if desired, any suitable organic solvent at the start up of a continuous process (e.g., aldehyde or aldehyde trimers being preferred), the primary organic solvent will in time normally eventually comprise both aldehyde products and higher boiling aldehyde liquid condensation by-products due to the nature of such continuous processes. Such aldehyde condensation by-products can also be preformed if desired and used accordingly, and methods for their preparation are more fully described, e.g., in U.S. Pat. Nos. 4,148,830 and 4,247,486. Of course, it is obvious that the amount of organic solvent employed is not critical to the subject invention and need only be that amount sufficient to provide the reaction medium with the particular Group VIII transition metal and dissolved ligand concentrations desired for a given process. In general, the amount of organic solvent may range from about 5 percent by weight up to about 95 percent by weight or more based on the total weight of the reaction medium.

It is further generally preferred to carry out the hydroformylation process of this invention in a continuous manner. Such types of continuous processes are well known in the art and may involve e.g., hydroformylating the olefinic starting material with carbon monoxide and hydrogen in a non-aqueous liquid homogeneous reaction medium comprising the olefin, aldehyde product, higher boiling aldehyde condensation by-products, the Group VIII transition metal-monosulfonated tertiary phosphine salt ligand complex catalyst, and free monosulfonated tertiary phosphine salt ligand; supplying make-up quantities of the olefinic starting material, carbon monoxide and hydrogen to the reaction medium; maintaining reaction temperature and pressure conditions favorable to the hydroformylation of the olefinic starting material; and recovering the desired aldehyde hydroformylation product in any conventional manner desired. While the continuous process can be carried out in a single pass mode, i.e., wherein a vaporous mixture comprising unreacted olefinic starting material and vaporized aldehyde product is removed from the liquid reaction medium from whence the aldehyde product is recovered and make up olefinic starting material, carbon monoxide and hydrogen are supplied to the liquid reaction medium for the next single pass through without recycling the unreacted olefinic starting material, it is generally desirable to employ a continuous process that involves either a liquid and/or gas recycle procedure. Of course it is to be understood that continuous processes involving solely a gas recycle procedure are not readily suitable for hydroformylating higher olefins of, e.g., $C_6$ to $C_{20}$ carbon atoms due to the low volability of their aldehyde products. Such types of recycle procedures are well known in the art and may involve the liquid recycling of the Group VIII transition metal-monosulfonated tertiary phosphine salt ligand complex catalyst solution separated from the desired aldehyde reaction product or a gas recycle procedure, or a combination of both a liquid and gas recycle procedure such as disclosed, e.g., in U.S. Pat. Nos. 4,148,830; 4,247,486 and 4,593,127, if desired. The most preferred hydroformylation process of this invention comprises a continuous liquid rhodium catalyst recycle process.

The desired aldehyde product may be recovered in any conventional manner such as described, e.g., in U.S. Pat. Nos. 4,148,830; 4,247,486 and 4,593,127. For instance, in a continuous liquid catalyst recycle process the portion of the liquid reaction solution (containing aldehyde product, catalyst, etc.) removed from the reactor can be passed to a vaporizer/separator wherein the desired aldehyde product can be separated via distillation, in one or more stages, under normal, reduced or elevated pressure, from the liquid reaction solution, condensed and collected in a product receiver, and further purified if desired. The remaining non-volatilized catalyst containing liquid reaction solution may then be recycled back to the reactor as may if desired any other volatile materials, e.g., unreacted olefin, and any hydrogen and carbon monoxide dissolved in the liquid reaction solution after separation thereof from the condensed aldehyde product, e.g., by distillation in any conventional manner. In general, it is preferred to separate the desired aldehyde product from the rhodium catalyst containing product solution by vaporization under reduced pressure and at temperatures such as below 150° C. and more preferably below 130° C.

As noted above, the hydroformylation process of this invention is carried out in the presence of free monosulfonated tertiary phosphine salt ligand, i.e., ligand that is not complexed with the Group VIII transition metal of the metal complex catalyst employed and the free monosulfonated tertiary phosphine salt ligand may correspond to any of the above defined monosulfonated tertiary phosphine salt ligands discussed above. Thus the hydroformylation process of this invention may be carried out in any excess amount of free ligand desired, e.g., at least one mole of free monosulfonated tertiary phosphine salt ligand per mole of Group VIII transition metal present in the reaction medium. In general amounts of free ligand of from about 4 to about 300, and preferably from about 10 to about 200 moles per mole of Group VIII transition metal (e.g., rhodium) present in the reaction medium should be suitable for most purposes, particularly with regard to rhodium catalyzed hydroformylation. Of course, if desired, make up monosulfonated tertiary phosphine salt ligand can be supplied to the reaction medium of the hydroformylation process, at any time and in any suitable manner, to maintain a predetermined level of free ligand in the reaction medium, if desired.

The reaction conditions for effecting the hydroformylation process of this invention may be those heretofore conventionally used and may comprise a reaction temperature of from about 45° C. to about 200° C. and pressures ranging from about 1 to 10,000 psia.

Of course, it is to be understood that while the optimization of the reaction conditions necessary to achieve the best results and efficiency desired are dependent upon one's experience in the utilization of the subject hydroformylation invention, only a certain measure of experimentation should be necessary to ascertain those conditions which are optimum for a given situation and such should be well within the knowledge of one skilled in the art and easily obtainable by following the more preferred aspects of this invention as explained herein and/or by simple routine experimentation.

For instance, the total gas pressure of hydrogen, carbon monoxide and olefinic unsaturated starting compound of the hydroformylation process of this invention may range from about 1 to about 10,000 psia. More preferably, however, in the hydroformylation of olefins to produce aldehydes it is preferred that the process be operated at a total gas pressure of hydrogen, carbon monoxide and olefinic unsaturated starting compound of less than about 1500 psia. and more preferably less than about 500 psia. The minimum total pressure of the reactants is not particularly critical and is limited predominately only by the amount of reactants necessary to obtain a desired rate of reaction. More specifically the carbon monoxide partial pressure of the hydroformylation process of this invention is preferably from about 1 to about 120 psia and more preferably from about 3 to about 90 psia, while the hydrogen partial pressure is preferably about 15 to about 160 psia and more preferably from about 30 to about 100 psia. In general $H_2:CO$ molar ratio of gaseous hydrogen to carbon monoxide may range from about 1:10 to 100:1 or higher, the preferred hydrogen to carbon monoxide molar ratio being from about 1:1 to about 50:1.

Further as noted above the hydroformylation process of this invention may be conducted at a reaction temperature from about 45° C. to about 200° C. The preferred reaction temperature employed in a given process will of course be dependent upon the particular olefinic starting material and metal catalyst employed as well as the efficiency desired. In general, it is preferred to employ a reaction temperature of from about 60° C. to about 140° C. in rhodium catalyzed hydroformylation processes.

Finally, the aldehyde products of the hydroformylation process of this invention have a wide range of utility that is well known and documented in the prior art, e.g., they are especially useful as starting materials for the production of alcohols and acids.

The beneficial factors involved in the employment of the monosulfonated tertiary phosphine salt ligands in this invention are many as described above, not the least of which is the wide processing latitude afforded one in selecting the proper combination of conditions that will be most useful in obtaining or at least best approaching a particular desired result or need. For instance the monosulfonated tertiary phosphine salt ligands can be used as the phosphorus ligand in non-agueous rhodium catalyzed hydroformylation processes designed to produce aldehydes from both low as well as high molecular weight olefins at highly acceptable catalytic activity rates at even conventional preferred low hydroformylation pressures and/or low rhodium concentrations without unduly sacrificing processing efficiency and/or catalyst stability. Moreover the low volatility of the water insoluble monosulfonated tertiary phosphine salt ligands of this invention (such salts are virtually non volatile, i.e., they normally will decompose before they can be volatilized) render them especially suitable as a means for minimizing the undue ligand and/or catalyst loss that can be experienced during the aldehyde product separation (via distillation) of low volatile aldehydes derived from high molecular weight olefins (e.g., $C_6$, to $C_{20}$ carbon atoms) when conventional higher volatile phosphorus ligands are employed. Moreover the discovery of a suitable ligand, such as the monosulfonated tertiary phosphine salt ligands of this invention, which may be employed to provide a metal-phosphorus complex catalyst for the hydroformylation of both low molecular weight as well as high molecular weight, olefins clearly minimizes ligand and/or catalyst inventory storage problems and may possibly even do away with any need at all to switch ligands and/or catalyst, when one desires to change a commercial operation from one that has been producing low molecular weight aldehydes from low molecular weight olefins (e.g., $C_2$ to $C_5$ olefins) to one that is to produce high molecular weight aldehydes from high molecular weight olefins (e.g., $C_6$ to $C_{20}$ olefins). Further, the organic solubility of the monosulfonated tertiary phosphine salt ligands employable in this invention allows the non-agueous hydroformylation process of this invention to be readily retrofitted to existing non-aqueous hydroformylation design apparatus and eguipment, without the need for major modifications of same.

It has further been surprisingly observed that the normal (straight) chain to isomer (branched) chain aldehyde product ratio of the hydroformylation process of this invention may be varied and controlled over a wide range by simply varying the type and size of the cation group of such ligands.

The following examples are illustrative of the present invention and are not to be regarded as limitative. It is to be understood that all of the parts, percentages and proportions referred to herein and in the appended claims are by weight unless otherwise indicated.

EXAMPLE 1

A series of various rhodium complex catalyst precursor solutions consisting essentially of the solubilized reaction product of rhodium dicarbonyl acetylacetonate and various triphenylphosphine monosulfonic acid salt ligands were prepared and employed to hydroformylate propylene into $C_4$ aldehydes in the following manner.

Rhodium dicarbonyl acetylacetonate was mixed at ambient temperature with various triphenylphosphine monosulfonated salt ligands having the formula:

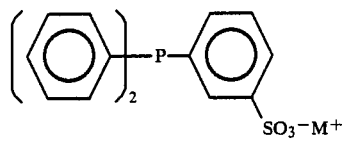

wherein M+ represents a radical as shown in TABLE 1 below, and sufficient Texanol ® (2,2,4 -trimethyl-1,3-pentanediol monoisobutyrate) as the solvent to produce the various rhodium catalytic precursor solutions containing the amounts of rhodium and ligands shown in TABLE 1 below.

Each rhodium catalytic precursor solution so prepared was then employed to hydroformylate propylene in a magnetically stirred, 100 mL capacity, stainless steel autoclave which was attached to a gas manifold for introducing gases to the desired partial pressures. The autoclave was also eguipped with a pressure calibrator for determining reaction pressure to ±0.01 psia. and a platinum resistance thermometer for determining reactor solution temperatures to ±0.10° C. The reactor was heated externally by two 300 watt heating bands. The reactor solution temperature was controlled by a platinum resistance sensor connected to an external proportional temperature controller for controlling the temperature of the external band heaters.

In each non-agueous hydroformylation reaction, about 15 milliliters (about 14 grams) of the rhodium catalytic precursor solution so prepared was charged to the autoclave reactor under nitrogen and heated to the reaction temperature employed (as given in Table 1 below). The reactor was then vented down to 5 psig. and a premixed gas mixture of 1:1:1 carbon monoxide:-hydrogen:propylene was introduced into the reactor via the gas manifold (partial pressures given in Table 1) and the propylene so hydroformylated.

The hydroformylation reaction rate in gram moles per liter per hour of $C_4$ aldehydes produced was determined from seguential 5 psia. pressure drops in the reactor spanning the nominal operating pressure in the reactor, while the mole ratio of linear (n-butyraldehyde) to branched (2 -methylpropionaldehyde) product was measured by gas chromatography and the results are given in Table 1 below.

TABLE 1

| Run No. | Ligand ($M^+$ =) | Reaction Rate G moles/L/hr | Linear/ Branched Aldehyde Mole Ratio |
|---|---|---|---|
| 1 | $N^+H (C_8H_{17})_3$ | $0.42^a$ | 4.2 |
| 2 | $N^+H (CH_3)_2(C_{12}H_{25})$ | $0.31^a$ | 6.5 |
| 3 | $N^+H (CH_3)_2(C_8H_{17})$ | $0.37^a$ | 6.4 |
| 4 | $N^+H (CH_3)_2(C_8H_{17})$ | $0.29^b$ | 8.6 |
| 5 | $N^+H (CH_3)_2(C_{16}H_{33})$ | $0.25^a$ | 6.3 |

$^a$Reaction Conditions:
100° C., 200 ppm Rhodium; about 118 mole equivalents of ligand per mole of rhodium; 60 psia 1:1:1 $H_2:CO:C_3H_6$
$^b$Reaction Conditions:
100° C., 200 ppm Rhodium; about 196 mole equivalents of ligand per mole of rhodium; 90 psia 1:1:1 $H_2:CO:C_3H_6$.

EXAMPLE 2

The same procedure and conditions employed in Example 1 of preparing a rhodium catalytic precursor solution using rhodium dicarbonyl acetyl acetonate, Texanol ® as solvent and various cyclohexyldiphenyl-phosphine monosulfonated salt ligands having the formula:

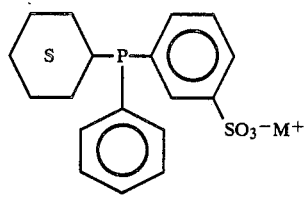

wherein $M^+$ represents a guaternary trioctyl- or dimethyldodecyl-ammonium radical as given in Table 2 below, and hydroformylating propylene was repeated employing the rhodium complex catalyst precursor solutions and hydroformylation reaction conditions as shown in Table 2 below. The hydroformylation reaction rate in terms of gram moles per liter per hour of $C_4$ aldehydes produced as well as the mole ratio of linear (n-butyraldehyde) to branched (2-methyl propionaldehyde) product were determined as in Example 1 and the results are given in Table 2 below.

TABLE 2

| Run No. | Ligand ($M^+$ =) | Reaction Rate G moles/L/hr | Linear/ Branched Aldehyde Mole Ratio |
|---|---|---|---|
| 1 | $N^+H (C_8H_{17})_3$ | 1.95 | 1.57 |
| 2 | $N^+H (CH_3)_2(C_{12}H_{25})$ | 1.11 | 1.66 |

Reaction Conditions:
100° C., 200 ppm Rhodium; about 20 mole equivalents of ligand per mole of rhodium; 60 psia 1:1:1 $H_2:CO:C_3H_6$.

EXAMPLE 3

The same procedure and conditions employed in Example 1 of preparing a rhodium catalytic precursor solution using rhodium dicarbonyl acetyl acetonate, Texanol ® as solvent and various dicyclohexylphenyl-phosphine monosulfonated salt ligands having the formula:

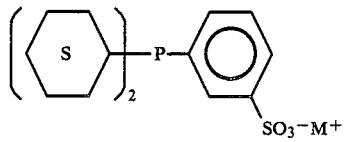

wherein $M^+$ represents a quaternary trioctyl- or dimethyldodecyl-ammonium radical as given in Table 3 below, and hydroformylating propylene, was repeated employing the rhodium complex catalyst precursor solutions and hydroformylation reaction conditions as shown in Table 3 below. The hydroformylation reaction rate in terms of gram moles per liter per hour of $C_4$ aldehydes produced as well as the mole ratio of linear (n-butyraldehyde) to branched (2-methyl propionaldehyde) product were determined as in Example 1 and the results are given in Table 3 below.

TABLE 3

| Run No. | Ligand ($M^+$ =) | Reaction Rate G moles/L/hr | Linear/ Branched Aldehyde Mole Ratio |
|---|---|---|---|
| 1 | $N^+H (C_8H_{17})_3$ | 0.82 | 1.13 |
| 2 | $N^+H (CH_3)_2(C_{12}H_{25})$ | 0.88 | 1.14 |

Reaction Conditions:
100° C.; 200 ppm Rhodium; about 20 mole equivalents of ligand per mole of rhodium; 60 psia 1:1:1 $H_2:CO:C_3H_6$.

EXAMPLE 4

The same procedure and conditions employed in Example 1 of preparing a rhodium catalytic precursor solution using rhodium dicarbonyl acetyl acetonate, Texanol ® as solvent and monosulfonated tertiary phosphine salt and hydroformylating butene-1, was repeated employing the rhodium complex catalyst precursor solutions and hydroformylation reaction conditions as shown in Table 4 below. The monosulfonated tertiary phosphine salt ligand employed in Run No. 1 was a trioctyl ammonium sulfonated cyclohexyldi-phenylphosphine (CHDPMS) having the formula

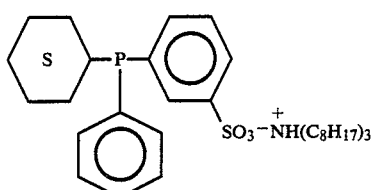

while the ligand used in Run No. 2 was a trioctyl ammonium sulfonated dicyclohexylphenylphosphine (DCHPPS) having the formula

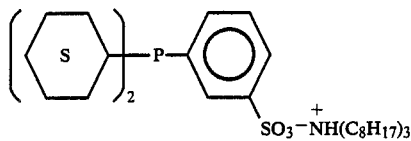

The hydroformylation reaction rate in terms of gram moles per liter per hour of $C_5$ aldehydes produced as well as the mole ratio of linear (n-valeraldehyde) to branched (2-methyl butyraldehyde) product were determined as in Example 1 and the results are given in Table 4 below.

TABLE 4

| Run No. | Ligand | Reaction Rate G moles/L/hr | Linear/ Branched Aldehyde Mole Ratio |
|---|---|---|---|
| 1 | CHDPMS | 11.62 | 2.54 |
| 2 | DCHPPMS | 3.77 | 1.73 |

Reaction Conditions:
90° C.; 220 ppm Rhodium; about 20 mole equivalents of ligand per mole of rhodium; 80 psia 1:1:1 $H_2$:CO and 44 psia butene-1.

EXAMPLE 5

The same procedure and conditions employed in Example 1 of preparing a rhodium catalytic precursor solution using rhodium dicarbonyl acetyl acetonate, Texanol ® as solvent and monosulfonated triphenylphosphine ligand having the formula

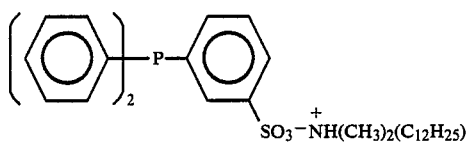

and hydroformylating dodecene-1 was repeated employing the various rhodium complex catalyst precursor solutions and various hydroformylation reaction conditions as shown in Table 5 below. The hydroformylation reaction rate in terms of gram moles per liter per hour of $C_{13}$ aldehydes produced as well as the mole ratio of linear (tridecanal) to branched (2-methyl dodecanal) product were determined as in Example 1 and the results are given in Table 5 below.

TABLE 5

| Run No. | Rh ppm | Temp °C. | Ligand/ Rhodium Mole Ratio | Partial CO psia | Pressures $H_2$ psia | Olefin Dodecene-1 ml | Reaction Rate Gram/Moles L/Hr | Linear/ Branched Aldehyde Mole Ratio |
|---|---|---|---|---|---|---|---|---|
| 1 | 25 | 100 | 10 | 22 | 44 | 2.5 | 0.53 | 3.2 |
| 2 | 25 | 100 | 10 | 22 | 44 | 5.0 | 1.37 | 3.7 |
| 3 | 200 | 120 | 200 | 22 | 44 | 5.0 | 3.76 | 11.8 |
| 4 | 500 | 70 | 50 | 22 | 44 | 5.0 | 0.93 | 13.9 |
| 5 | 200 | 100 | 100 | 10 | 40 | 5.0 | 2.04 | 16.7 |
| 6 | 200 | 100 | 100 | 100 | 40 | 5.0 | 2.88 | 5.1 |

EXAMPLE 6

Continuous hydroformylation of butene-1 using a monosulfonated triphenylphosphine salt ligand was conducted in the following manner.

The non-aqueous hydroformylation was conducted in a glass reactor operating in a continuous single pass butene-1 hydroformylation mode. The reactor consisted of a three ounce pressure bottle submersed in an oil bath with a glass front for viewing. About 20-mL of a freshly prepared rhodium catalytic precursor solution was charged to the reactor with a syringe, after purging the system with nitrogen. The precursor solution contained about 300 ppm rhodium introduced as rhodium dicarbonyl acetylacetonate, about 15 weight percent (about 80 mole equivalents of ligand per mole of rhodium) of a monosulfonated triphenylphosphine salt ligand of the formula

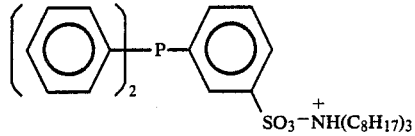

and Texanol ® as the solvent. After closing the reactor, the system was again purged with nitrogen and the oil bath was heated to furnish the desired hydroformylation reaction temperature. The hydroformylation reaction was conducted at a total gas pressure of about 160 psig., the partial pressures of hydrogen, carbon monoxide, and butene-1 being given in Table 6 below, the remainder being nitrogen and aldehyde product.

The flows of the feed gases (carbon monoxide, hydrogen, butene-1 and nitrogen) were controlled individually with mass flow meters and the feed gases dispersed into the precursor solution via microporous stainless steel spargers. The reaction temperatures are given in Table 6 below. The unreacted portion of the feed gases was stripped out with the product $C_5$ aldehydes and the outlet gas analyzed over about 14 days of continuous operation. The approximate daily average reaction rates, in terms of gram moles per liter per hour of product $C_5$ aldehydes, as well as the linear (n-valeraldehyde) to branched (2-methyl-butyr-aldehyde) product ratio are given in Table 6 below.

TABLE 6
TEST RESULTS - DAILY AVERAGES

| Days Opern | Temp °C. | Rhodium* ppm | Ligand* wt. % | Partial Pressures | | | Rate g moles/ L/Hr | Linear/ Branched Aldehyde Mole Ratio |
|---|---|---|---|---|---|---|---|---|
| | | | | CO | H2 | C4H8 | | |
| 0.9 | 85 | 261 | 13.05 | 21 | 58 | 2 | 0.75 | 7.43 |
| 1.9 | 83 | 264 | 13.2 | 18 | 56 | 3 | 1.82 | 9.42 |
| 3.0 | 70 | 269 | 13.4 | 17 | 57 | 3 | 1.32 | 9.29 |
| 3.9 | 70 | 278 | 13.9 | 17 | 57 | 3 | 1.27 | 9.28 |
| 4.8 | 70 | 287 | 14.3 | 17 | 57 | 3 | 1.21 | 9.41 |
| 6.0 | 70 | 296 | 14.8 | 18 | 58 | 3 | 1.07 | 11.41 |
| 6.8 | 70 | 249 | 12.4 | 13 | 54 | 7 | 2.24 | 8.60 |
| 7.9 | 70 | 265 | 13.2 | 16 | 56 | 6 | 2.04 | 9.73 |
| 9.0 | 83 | 289 | 14.4 | 16 | 56 | 6 | 1.81 | 10.33 |
| 9.4 | 85 | 301 | 15.0 | 16 | 56 | 6 | 1.82 | 10.82 |
| 11.8 | 85 | 321 | 16.0 | 17 | 56 | 6 | 1.67 | 13.12 |
| 12.8 | 85 | 334 | 16.7 | 16 | 56 | 7 | 1.98 | 12.17 |
| 13.8 | 85 | 341 | 17.0 | 16 | 56 | 7 | 2.20 | 11.76 |

*Changing values reflect change in daily liquid reactor solution levels.

EXAMPLE 7

Butene-1 was continuously hydroformylated in the same manner as Example 6 using a catalyst precursor solution containing about 300 ppm rhodium introduced as rhodium dicarbonyl acetylacetonate, Texanol® as solvent, and about 11 weight percent (about 80 mole equivalents of ligand per mole of rhodium) of a monosulfonated triphenylphosphine salt ligand having the formula

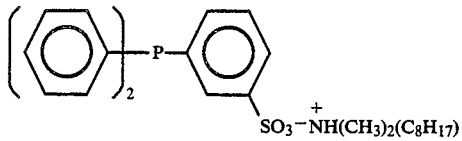

and the reaction conditions given in Table 7 below.

The approximate catalyst composition and daily average reaction rates, in terms of gram moles per liter per hour of product $C_5$ aldehydes, as well as the linear (n-valeraldehyde) to branched (2-methyl- butyraldehyde) product ratio are given in Table 7 below.

EXAMPLE 8

Butene-1 was continuously hydroformylated in the same manner as Example 6 using a catalyst precursor solution containing about 300 ppm rhodium introduced as rhodium dicarbonyl acetylacetonate, Texanol® as solvent, and about 12 weight percent (about 80 mole equivalents of ligand per mole of rhodium) of a monosulfonated triphenylphosphine salt ligand having the formula

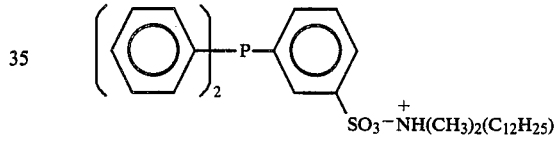

and the reaction conditions given in Table 8 below.

The approximate catalyst composition and daily average reaction rates, in terms of gram moles per liter per hour of product $C_5$ aldehydes, as well as the linear (n-valeraldehyde) to branched (2-methylbutyraldehyde) product ratio are given in Table 8 below.

TABLE 7
TEST RESULTS - DAILY AVERAGES

| Days Opern | Temp °C. | Rhodium* ppm | Ligand* wt. % | Partial Pressures (psia) | | | Rate g moles/ L/Hr | Linear/ Branched Aldehyde Mole Ratio |
|---|---|---|---|---|---|---|---|---|
| | | | | CO | H2 | C4H8 | | |
| 1.0 | 85 | 264 | 9.7 | 16 | 56 | 6 | 1.04 | 20.89 |
| 1.7 | 85 | 255 | 9.3 | 15 | 55 | 8 | 1.41 | 22.78 |
| 2.9 | 70 | 248 | 9.1 | 3 | 59 | 10 | 0.45 | 6.82 |
| 4.0$^a$ | 70 | 248 | 9.1 | 0 | 61 | 10 | — | — |
| 4.8$^a$ | 70 | 248 | 9.1 | 0 | 60 | 10 | — | — |
| 6.0 | 70 | 311 | 11.4 | 12 | 44 | 7 | 0.75 | |
| 6.8 | 70 | 260 | 9.5 | 13 | 56 | 8 | 1.66 | 22.01 |
| 8.0 | 70 | 256 | 9.3 | 15 | 57 | 9 | 1.56 | 22.72 |
| 8.8 | 82 | 266 | 9.7 | 15 | 57 | 9 | 1.40 | 22.42 |
| 9.4 | 85 | 278 | 10.2 | 15 | 60 | 9 | 1.28 | 25.69 |
| 11.8$^b$ | 85 | 294 | 10.8 | 16 | 64 | 9 | 0.81 | — |
| 12.8$^b$ | 85 | 309 | 11.3 | 16 | 57 | 10 | 0.79 | — |
| 13.7$^b$ | 85 | 303 | 11.1 | 16 | 57 | 12 | 0.68 | — |

*Changing values relfect change in daily liquid reactor solution levels.
$^a$Malfunction in mass flow meter for carbon monoxide stopped CO feed and prevented aldehyde product from being formed. It was fixed and the reaction continued.
$^b$Malfunction in gas chromatograph prevented accurate N/I aldehyde mole ratio readings which renders rate results suspect.

TABLE 8
TEST RESULTS - DAILY AVERAGES

| Days Opern | Temp °C. | Rhodium* ppm | Ligand* wt. % | Partial Pressures (psia) | | | Rate g moles/ L/Hr | Linear/ Branched Aldehyde Mole Ratio |
|---|---|---|---|---|---|---|---|---|
| | | | | CO | H2 | C4H8 | | |
| 1.0 | 85 | 275 | 10.9 | 15 | 56 | 7 | 1.46 | 16.91 |
| 2.0 | 83 | 260 | 10.4 | 15 | 56 | 8 | 1.78 | 16.79 |
| 3.0 | 70 | 266 | 10.6 | 15 | 56 | 8 | 1.62 | 19.03 |
| 4.0 | 70 | 276 | 10.9 | 15 | 56 | 8 | 1.54 | 21.59 |
| 4.8 | 70 | 285 | 11.5 | 16 | 56 | 8 | 1.53 | 21.80 |
| 5.8 | 70 | 290 | 11.6 | 15 | 56 | 9 | 1.61 | 21.98 |
| 6.8 | 70 | 295 | 11.8 | 15 | 56 | 9 | 1.57 | 22.45 |
| 8.0 | 70 | 300 | 12.0 | 15 | 56 | 9 | 1.60 | 22.60 |
| 9.0 | 82 | 304 | 12.1 | 15 | 55 | 10 | 1.64 | 22.18 |
| 9.4 | 85 | 309 | 12.3 | 10 | 41 | 15 | 2.86 | 12.63 |
| 11.8 | 85 | 309 | 12.3 | 8 | 49 | 14 | 4.34 | 4.74 |
| 12.6 | 85 | 435 | 17.4 | 16 | 55 | 11 | 2.23 | 8.15 |

*Changing values relfect change in daily liquid reactor solution levels.

EXAMPLE 9

In a continuous catalyst liguid recycle manner, an olefin starting material of octene-1 was hydroformylated for nine days as follows.

The liquid recycle reactor system employed contained two 2.8 liter stainless steel stirred tank reactors, connected in series, each containing a vertically mounted agitator and a circular tubular sparger near the bottom of the reactor for feeding the syn gas. The sparger contained a plurality of holes of sufficient size to provide the desired gas flow into the liquid body. Reactor 1 contained a silicone oil shell as means of bringing the contents of the reactors up to reaction temperature while the reaction solution in Reactor 2 was heated by an electrical heater. Both reactors contained internal cooling coils for controlling the reaction temperature. Reactors 1 and 2 were connected via a line to transfer any unreacted gases from reactor 1 to reactor 2 and were further connected via a line so that a portion of the liquid reaction solution containing aldehyde product and catalyst from reactor 1 could be pumped into reactor 2 wherein the unreacted olefin of reactor 1 is further hydroformylated in reactor 2.

Each reactor also contained a pneumatic liquid level controller for automatic control of the liquid levels in the reactors. Reactor 1 further contained a line for introducing the liquid olefin using a metering pump, and a line for introducing syn gas through the sparger, while make up syn gas was added to reactor 2 via the same transfer line carrying the unreacted syn gas from reactor 1. Reactor 2 also contained a blow off vent for removal of the unreacted gases. A line from the bottom of reactor 2 was connected to the top of a vaporizer so that a portion of the liquid reaction solution could be pumped from reactor 2 to the vaporizer. The vaporizer was maintained at reduced pressure with the help of a vacuum pump. Vaporized aldehyde was disengaged from the non-volatilized components of the liquid reaction solution in the gas-liquid separator part of the vaporizer. The remaining non volatilized catalyst containing liquid reaction solution was pumped through a recycle line back into reactor 1. The recycle line also contained a pneumatic liquid level controller. The vaporized aldehyde product was passed into a water-cooled condenser, liquified and collected in a product receiver.

The hydroformylation reaction was conducted by charging about 0.779 liters of a catalyst precursor solution of rhodium dicarbonyl acetylacetonate (about 300 ppm rhodium), about 23 wt. % of 3-(diphenylphosphine)-benzenesulfonic acid, trioctylammonium salt ligand having the formula

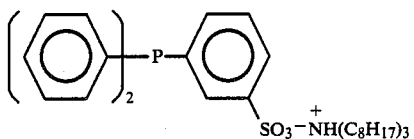

(about 120 mole equivalents of ligand per mole of rhodium) and about 77 wt. % of $C_9$ aldehyde as solvent to reactor 1. About 1.00 liters of the same catalyst precursor solution was charged to reactor 2. The reactor system was then purged with nitrogen to remove any oxygen present, and the reactors heated to their reaction temperatures given in Table 9 below. Controlled flows of purified hydrogen and carbon monoxide were fed through the sparger into the bottom of reactor 1 and the reactor pressure increased to the operating pressure given in Table 9 below. When the liquid level in reactor 1 started to increase as a result of the pumping of liquid octane-1 and its conversion to liquid aldehyde product, a portion of the liquid reaction solution of reactor 1 was pumped into reactor 2 through a line into the top of reactor 2 at a rate sufficient to maintain a constant liquid level in reactor 1. The pressure of reactor 2 increased to its operating pressure given in Table 9 below. Blow off gas from reactor 2 was analyzed and measured. A controlled flow of make-up syn gas (CO and $H_2$) was added to reactor 2 in order to maintain their desired partial pressures in reactor 2. The operating pressures and reaction temperatures were maintained throughout the hydroformylation. As the liquid level in reactor 2 started to increase as a result of the pumping from reactor and the liquid aldehyde product formation, a portion of the liquid reaction solution was pumped to the vaporizer/ separator at a rate sufficient to maintain a constant liquid level in reactor 2. The crude aldehyde product was separated at 125° C. and about 40 mm Hg pressure from the liquid reaction solution, condensed and collected in a product receiver. The remaining non volatilized catalyst containing liquid reaction solution was recycled back to reactor 1.

The hydroformylation of said octene-1 was carried out continuously for nine days.

The hydroformylation reaction conditions as well as the rate of $C_9$ aldehydes produced in terms of gram moles per liter per hour and the linear to branched aldehyde product ratio of nonanal to 2-methyloctanal are given in Table 9 below.

TABLE 9

| Days of Operation | 2 | 6 | 9 |
|---|---|---|---|
| Octene-1 feed, mole % | | | |
| Octene-1 | 98.28 | 98.28 | 98.28 |
| Octene-2 | 1.54 | 1.54 | 1.54 |
| Octane | 0.17 | 0.17 | 0.17 |
| Reactor No. 1 | | | |
| Temperature | 80.5 | 80.4 | 80.5 |
| Pressure, psia | 91.2 | 91.7 | 91.7 |
| H$_2$, psia | 70.6 | 67.9 | 83.0 |
| CO, psia | 16.5 | 20.7 | 6.3 |
| Octene-1 mole % | 9.0 | 9.8 | 8.8 |
| Octene-2 mole % | 4.1 | 2.6 | 4.9 |
| Reactor No. 2 | | | |
| Temperature | 90.4 | 90.4 | 90.6 |
| Pressure, psia | 82.7 | 84.7 | 83.7 |
| H$_2$, psia | 54.9 | 62.4 | 75.0 |
| CO, psia | 25.4 | 19.3 | 6.0 |
| Octene-1 mole % | 1.0 | 1.2 | 1.2 |
| Octene-2 mole % | 3.3 | 2.3 | 4.5 |
| Results | | | |
| C$_9$ Aldehydes/ g moles/L/hr | 1.16 | 1.14 | 1.07 |
| Linear/Branched Aldehyde Ratio | 6.3 | 5.5 | 12.3 |

EXAMPLE 10

Octene-1 was again continuously hydroformylated over a nine day period using a catalyst precursor solution of rhodium dicarbonyl acetylacetonate (about 330 ppm rhodium), about 22.8 wt. % of 3-(diphenylphosphine) - benzenesulfonic acid, trioctylammonium salt ligand (about 100 mole equivalents of ligand per mole of rhodium) and about 77 wt. % of C$_9$ aldehyde as solvent and the same hydroformylation procedure as described in Example 9 above. C$_9$ nonanal aldehyde product samples produced at various daily stages of the continuous process were analyzed for atomic phosphorus and rhodium content via inductively coupled plasma spectroscopy and the results are shown in Table 10 below.

TABLE 10

| Day of Operation | Phosphorus (ppm) | Rhodium (ppm) |
|---|---|---|
| 3 | 8.8 | <1 |
| 5 | 22.0 | <1 |
| 6 | 25.0 | <1 |
| 9 | 22.0 | — |

The above results show virtually no rhodium and very little phosphorus in the aldehyde (nonanal) product.

Various modifications and variations of this invention will be obvious to a worker skilled in the art and it is to be understood that such modifications and variations are to be included within the purview of this application and the spirit and scope of the appended claims.

What is claimed is:

1. In a non-aqueous hydroformylation process for producing aldehydes which comprises reacting an olefinically unsaturated organic compound with carbon monoxide and hydrogen, in a non-aqueous hydroformylation reaction medium containing an organic solubilized Group VIII transition metal-phosphorus ligand complex catalyst and free phosphorus ligand, wherein the hydroformylation reaction conditions comprise a reaction temperature of from about 45° C. to about 200° C., a total gas pressure of hydrogen, carbon monoxide and olefinically unsaturated compound of less than about 1500 psia; wherein the H$_2$:CO molar ratio of gaseous hydrogen to carbon monoxide is in the range of from about 1:10 to 100:1; and wherein said reaction medium contains at least about 4 moles of total free phosphorus ligand per mole of Group VIII transition metal in said medium, the improvement comprising employing as the phosphorus ligand of said complex catalyst and as said free phosphorus ligand, a low volatile, organic soluble monosulfonated tertiary phosphine salt the general formula

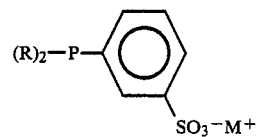

wherein each R group individually represents a radical containing from 1 to 30 carbon atoms selected from the class consisting of alkyl, aryl, alkaryl, aralkyl and cycloalkyl radicals and M represents an amine cation having the general formula

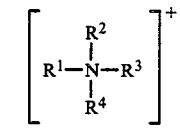

wherein R$^1$ represents hydrogen or a radical containing from 1 to 30 carbon atoms selected from the class consisting of alkyl, aryl, alkaryl, aralkyl, and cycloalkyl radicals, and each R$^2$, R$^3$ and R$^4$ group individually represents a radical selected from the class consisting of alkyl, aryl, alkaryl, aralkyl and cyclohexyl radicals, and wherein any two or three of said R$^1$, R$^2$, R$^3$ and R$^4$ groups can be bonded together to form a mono-, bi-, or poly-cyclic ring along with the nitrogen atom of said amine cation; with the proviso that in any given monosulfonated tertiary phosphine salt employed at least one of said R$^1$, R$^2$, R$^3$ and R$^4$ groups of the amine cation, M, represents an alkyl or aralkyl radical containing from 8 to 30 carbon atoms.

2. A process as defined in claim 1 wherein the H$_2$:CO molar ratio of gaseous hydrogen to carbon monoxide is in the range of from about 1:1 to about 50:1.

3. A process as defined in claim 1, wherein the Group VIII transition metal is rhodium, wherein the olefinically unsaturated compound contains from 2 to 20 carbon atoms, and wherein the reaction temperature is from about 60° C. to about 140° C.; wherein the total gas pressure of hydrogen, carbon monoxide and olefinically unsaturated compound is less than about 500 psia; wherein the carbon monoxide partial pressure is from about 1 to 120 psia; and the hydrogen partial pressure is from about 15 to 160 psia.

4. A process as defined in claim 3 wherein the olefinically unsaturated compound is an alpha olefin containing from 2 to 5 carbon atoms.

5. A process as defined in claim 4 wherein each R is individually a radical selected from the group consisting of a branched alkyl radical having from 3 to 9 carbon atoms, phenyl and cyclohexyl radicals.

6. A process as defined in claim 5, wherein R$_1$ is hydrogen or an alkyl radical containing from 1 to 20 carbon atoms, $R^2$ and $R^3$ are each individually alkyl radicals containing from 1 to 20 carbon atoms, and $R^4$ is an alkyl or aralkyl radical containing from 8 to 20 carbon atoms.

7. A process as defined in claim 6, wherein each R is individually a phenyl or cyclohexyl radical, $R^1$ is hydrogen, $R^2$ and $R^3$ are each individually alkyl radicals containing from 1 to 8 carbon atoms, and $R^4$ is an alkyl radical containing from 8 to 16 carbon atoms.

8. A process as defined in claim 7, wherein the alpha olefin is propylene or butene-1 and wherein $M^+$ represents a quaternary ammonium radical selected from the group consisting of trioctylammonium, dimethyldodecylammonium, dimethyloctylammonium, and dimethylcetylammonium.

9. A process as defined in claim 3, wherein the olefinically unsaturated compound is an alpha olefin containing from 6 to 20 carbon atoms.

10. A process as defined in claim 9, wherein the alpha olefin contains from 6 to 14 carbon atoms.

11. A process as defined in claim 10, wherein each R is individually a radical selected from the group consisting of a branched alkyl radical having from 3 to 9 carbon atoms, phenyl and cyclohexyl radicals.

12. A process as defined in claim 11, wherein $R^1$ is hydrogen or an alkyl radical containing from 1 to 20 carbon atoms, $R^2$ and $R^3$ are each individually alkyl radicals containing from 1 to 20 carbon atoms, and $R^4$ is an alkyl or aralkyl radical containing from 8 to 20 carbon atoms.

13. A process as defined in claim 12, wherein each R is individually a phenyl or cyclohexyl radical, $R^1$ is hydrogen, $R^2$ and $R^3$ are each individually alkyl radicals containing from 1 to 8 carbon atoms, and $R^4$ is an alkyl radical containing from 8 to 16 carbon atoms.

14. A process as defined in claim 13, wherein $M^+$ represents a quaternary ammonium radical selected from the group consisting of trioctylammonium, dimethyldodecylammonium, dimethyloctylammonium, and dimethylcetylammonium.

15. A process as defined in claim 14, wherein the alpha olefin is octene-1.

16. A process as defined in claim 10, wherein the monosulfonated tertiary phosphine salt ligand is 3-(diphenylphosphine) benzenesulfonic acid, trioctylammonium.

17. A process as defined in claim 16, wherein the alpha olefin is octene-1.

18. A process as defined in claim 16, wherein the alpha olefin is dodecene-1.

19. A process as defined in claim 10, wherein the hydroformylation process comprises a continuous catalyst containing liquid recycle procedure.

* * * * *